United States Patent [19]

Jiang

[11] Patent Number: 5,391,707
[45] Date of Patent: Feb. 21, 1995

US005391707A

[54] PROCESS FOR THE PRODUCTION OF DIOXANONE

[75] Inventor: Ying Jiang, North Haven, Conn.

[73] Assignee: United States Surgical Corporation, Norwalk, Conn.

[21] Appl. No.: 165,434

[22] Filed: Dec. 10, 1993

[51] Int. Cl.$^6$ .................. C08G 63/08; A61B 17/00
[52] U.S. Cl. ........................ 528/354; 525/411; 525/415; 528/361; 549/274; 606/228; 606/230
[58] Field of Search ............ 528/354, 361; 549/274; 606/228, 230; 525/411, 415

[56] References Cited

U.S. PATENT DOCUMENTS

| | | | |
|---|---|---|---|
| 2,142,033 | 12/1938 | McNamee et al. | 549/274 |
| 2,759,003 | 8/1956 | Jansen et al. | 549/263 |
| 2,900,395 | 8/1959 | Guest et al. | 549/274 |
| 3,000,906 | 9/1961 | Hasek et al. | 549/263 |
| 3,020,289 | 2/1962 | Welpert | 528/356 |
| 3,063,967 | 11/1962 | Schultz | 528/354 |
| 3,119,840 | 1/1964 | Mayheur et al. | 549/274 |
| 3,259,607 | 7/1966 | Cherdron et al. | 528/357 |
| 3,912,599 | 10/1975 | Dawes | 203/61 |
| 3,950,361 | 4/1976 | Taneda et al. | 549/263 |
| 4,052,988 | 10/1977 | Doddii et al. | 606/231 |
| 4,070,375 | 1/1978 | Suzuki | 549/274 |
| 4,643,191 | 2/1987 | Bezwada et al. | 606/230 |
| 4,646,741 | 3/1987 | Smith | 606/220 |
| 4,653,497 | 3/1987 | Bezwada et al. | 606/230 |
| 4,788,979 | 12/1988 | Jarrett et al. | 606/230 |
| 4,838,267 | 6/1989 | Jamiolkowski et al. | 606/224 |
| 5,007,923 | 4/1991 | Bezwada et al. | 606/231 |
| 5,023,350 | 6/1991 | Bhatia | 549/274 |
| 5,047,048 | 9/1991 | Bezwada et al. | 606/231 |
| 5,076,807 | 12/1991 | Bezwada et al. | 606/230 |
| 5,080,665 | 1/1992 | Jarrett et al. | 606/219 |

*Primary Examiner*—Samuel A. Acquah
*Assistant Examiner*—Shelley A. Dodson

[57] ABSTRACT

Processes of producing 1,4-dioxan-2-one (p-dioxanone) are improved by the addition of a blocking agent to a crude reaction product containing p-dioxanone. The blocking agent reacts with unreacted starting materials in the crude reaction product to protect the active sites thereon with groups that do not initiate polymerization of p-dioxanone. The polymerization of p-dioxanone before its recovery from the process is thereby inhibited.

23 Claims, No Drawings

PROCESS FOR THE PRODUCTION OF DIOXANONE

BACKGROUND OF INVENTION

This invention relates to an improvement in processes for the production of 1,4-dioxan-2-one (p-dioxanone). More particularly, this invention relates to a method for preventing the polymerization of p-dioxanone during processes of its production.

The dehydrogenation of DEG leads to the production of a mixture containing p-dioxanone and unreacted DEG. Pure p-dioxanone is recovered by distilling the mixture under heat and/or reduced pressure. It is well known that DEG initiates the polymerization of p-dioxanone at elevated temperatures. Specifically, the highly reactive hydrogens on DEG's hydroxyl groups function as polymerization initiators.

Several patents, e.g., U.S. Pat. Nos. 5,047,048 and 5,076,807, disclose examples in which DEG is specifically employed as a polymerization initiator. Because DEG tends to initiate polymerization of p-dioxanone at elevated temperatures, the distillation recovery-step results not only in the production of p-dioxanone monomer but in the production of low molecular weight polydioxanone as well. The polymerization of p-dioxanone, in turn, leads to a decrease in the yield of p-dioxanone monomer from the vapor phase dehydrogenation of DEG.

Polymers derived in whole or in part from p-dioxanone have found utility in the fabrication of absorbable medical/surgical devices, e.g., sutures, staples, clips, prostheses, etc. Examples of patents which disclose the polymerization of p-dioxanone alone or in combination with other monomers include, e.g., U.S. Pat. Nos. 4,052,988, 4,643,191, 4,646,741, 4,653,497, 4,788,979, 4,838,267, 5,007,923, 5,047,048, 5,076,807 and 5,080,665. In light of the important end-uses toward which p-dioxanone is employed, improvements in commercially utilized methods of producing p-dioxanone monomer are desired. It would therefore be advantageous to provide processes to prevent the polymerization of p-dioxanone prior to its recovery by distillation as well as to provide processes to facilitate the separation of p-dioxanone from other compounds during the distillation.

SUMMARY OF THE INVENTION

The present invention provides a process for producing dioxanone monomer wherein a blocking agent is added to a mixture of p-dioxanone monomer and residual reactants used to form the monomer. The blocking agent inhibits polymerization of the monomer by reacting with hydroxyl groups (or other active groups) which might otherwise serve as an initiator for polymerization. In a particularly useful embodiment, p-dioxanone is produced by dehydrogenating DEG in the presence of a metallic catalyst and, optionally, hydrogen gas at temperatures above about 200° C., to provide a mixture containing both p-dioxanone and unreacted DEG, adding a blocking agent to the mixture to inhibit the polymerization initiation activity of DEG, and distilling the condensate to obtain p-dioxanone.

The term "blocking agent" herein signifies any compound which reacts with active sites on any residual reactant or other compounds used to form the p-dioxanone, protecting them with groups that do not initiate the polymerization of p-dioxanone. The blocking agents (as added or as reacted with the residual reactants) must also not adversely affect p-dioxanone. For example, when DEG is used to form p-dioxanone, the blocking agent reacts with residual DEG to remove the reactive hydrogen on DEG's hydroxyl groups. The protected form of DEG, unlike DEG per se, does not initiate the polymerization of p-dioxanone. Thus, the yield of p-dioxanone monomer from the reaction is increased. In general, yields ranging from about 70% to about 90% have been obtained by the method of the present invention. In addition, the protected form of DEG possesses a higher boiling point relative to p-dioxanone than unprotected DEG and therefore is easier to separate from p-dioxanone during distillation.

DESCRIPTION OF THE PREFERRED EMBODIMENTS

The process of the present invention increases the amount of p-dioxanone monomer recovered from a crude reaction product containing p-dioxanone by inhibiting polymerization of p-dioxanone during distillation or other processing of the crude reaction product. The term "crude reaction product" is intended to embrace the mixture of materials produced during the production of p-dioxanone. Thus, the crude reaction product will not only contain p-dioxanone, but may also contain unreacted starting materials and other compounds employed in forming p-dioxanone.

The blocking agent employed herein is not limited to any one particular compound or class of compounds. Any compound can be employed as long as it protects the active groups on residual reactants with groups that do not function as polymerization initiators. The blocking agent, in its original form as added to the crude reaction product or in whatever form the agent attains after reacting with the residual reactants, should not be reactive towards p-dioxanone. Examples of such compounds include benzyl halide and dihalomethylbenzene, preferably benzyl bromide and dibromomethylbenzene. A mixture of benzyl bromide and pyridine in a weight ratio of 2:1 has been found to provide particularly good results.

The amount of blocking agent utilized can vary widely, i.e., from about 2 to about 25 weight percent based on the weight of the crude reaction product and its p-dioxanone content. The blocking agent can be added, either as a liquid or a solid, to the crude reaction product. Where a solid blocking agent is employed it must either be soluble in the crude reaction product or added with an appropriate solvent. Preferably the crude reaction-product is dried with sodium bicarbonate or any other suitable drying agent and filtered to remove any impurities before the blocking agent is added. The mixture of crude reaction product and blocking agent can be distilled under heat and reduced pressure to provide p-dioxanone in a greater yield than which would otherwise be obtained.

As noted earlier, when p-dioxanone is formed from the dehydrogenation of DEG, protecting the reactive hydrogens on DEG with unreactive groups leads to a significant decrease in the extent to which p-dioxanone is polymerized prior to separation and distillation. Furthermore, an additional benefit has been observed in that protected forms of DEG possess higher boiling points relative to p-dioxanone than DEG per se. Thus, it has been found that protected DEG is easier to separate from p-dioxanone during the distillation recovery process. By utilizing the blocking agents herein the inventors have succeeded in obtaining p-dioxanone in yields ranging from about 70% to about 90%.

The dehydrogenation of DEG is carried out in the presence of a metallic catalyst. Such catalyst can be a pure metal, e.g., copper, chromium, cobalt, iron, platinum, nickel, palladium, etc., or a mixture containing two or more metals, e.g., a copper-chromium mixture. A copper-chromium catalyst containing 27.4 percent copper and 44.9 percent chromium has been found to produce particularly good results and is preferred.

The temperature at which the dehydrogenation of DEG is carried out can vary widely, i.e., from about 200° C. to about 240° C. Preferably, the reaction is carried out at a temperature ranging from about 230° C. to about 235° C.

Polymers made from p-dioxanone have been employed in the manufacture of absorbable surgical devices. Such surgical devices should be fabricated from polymers possessing a very high degree of purity, i.e., purity of 99% and higher, since the polymers themselves decompose and become absorbed within the body. Thus, the distillate containing p-dioxanone can be further purified to obtain 99%+ pure p-dioxanone monomer. Methods of obtaining highly pure p-dioxanone from reaction products containing p-dioxanone include crystallization techniques, such as the processes disclosed in commonly owned copending U.S. Application Ser. No. 08/036,922, the disclosure of which is incorporated by reference herein. The method disclosed therein includes the steps of forming a solution by dissolving crude p-dioxanone in an aliphatic ester, forming p-dioxanone crystals from the solution to provide a mixture and filtering the mixture to recover pure p-dioxanone. The steps can be repeated to obtain p-dioxanone of very high purity, e.g., purity on the order of 99% and higher.

Dioxanone obtained by the method of this invention can be polymerized by itself or in combination with other copolymerizable monomers, e.g., glycolide, lactide, trimethylene carbonate, caprolactone, etc. The homopolymers and/or copolymers can be linear or branched and can be random, block or graft copolymers. The polymers and/or copolymers can be used in the fabrication of a wide variety of medical/surgical devices, e.g., sutures, staples, clips, pins, prostheses, etc. Processes for polymerizing p-dioxanone and forming surgical articles (such as sutures) therefrom are known to those skilled in the art. See, for example, U.S. Pat. No. 4,052,988 the disclosure of which is incorporated herein by reference.

The following example illustrates the practice of the present invention:

EXAMPLE 1

Diethylene glycol (2 kg) is placed into a reaction chamber which contains a copper chromium catalyst 2% of DEG composed of 27.4 parts by weight copper and 44.9 parts by weight chromium. A temperature of between 220° C. and 240° C. is maintained throughout the reaction. The resulting crude reaction product containing p-dioxanone and unreacted DEG is dried in molecular sieves (4 Angstroms) overnight and then filtered. The dried product is placed in a 3-necked flask and benzyl bromide (100 g) along with pyridine (50 g) are added to the flask. The resulting mixture is distilled under reduced pressure at a distillation rate of about 60 drops per minute. In this way, 1.6 kg of p-dioxanone is recovered.

Obviously, other modifications and variations of the present invention are possible in light of the above teachings. It is therefore to be understood that changes may be made in particular embodiments of the invention described which are within the full intended scope of the invention as defined by the claims.

What is claimed is:

1. A method of forming a surgical article comprising:
   (a) providing a crude reaction product comprising p-dioxanone;
   (b) adding a blocking agent to said crude reaction product to form a mixture;
   (c) distilling said mixture to recover p-dioxanone;
   (d) polymerizing said p-dioxanone to form a polymer; and
   (e) forming said polymer into a surgical article.

2. A method as in claim 1 wherein said crude reaction product further comprises diethylene glycol.

3. A method as in claim 1 wherein said blocking agent is selected from the group consisting of benzyl bromide and dibromomethylbenzene.

4. A method as in claim 1 wherein said polymer is bioabsorbable.

5. A method as in claim 1 wherein said polymer is a copolymer.

6. A method as in claim 5 wherein said copolymer is a block copolymer.

7. A method as in claim 6 wherein said block copolymer comprises a block made from a random copolymer containing p-dioxanone.

8. A method as in claim 1 wherein said step of providing a crude reaction product comprises dehydrogenating diethylene glycol.

9. A method as in claim 8 wherein said dehydrogenating step is carried out in the presence of a metallic catalyst.

10. A method as in claim 9 wherein said metallic catalyst comprises one or more metals selected from the group consisting of copper, chromium, cobalt, iron, platinum, nickel and palladium.

11. A method as in claim 10 wherein said metallic catalyst comprises copper and chromium.

12. A method as in claim 1 wherein said blocking agent is added in an amount from about 2 to about 25 percent by weight of the crude reaction product.

13. A method of forming a surgical article comprising:
   (a) forming a crude reaction product comprising p-dioxanone and diethylene glycol;
   (b) adding benzyl bromide to said crude reaction product to form a mixture;
   (c) distilling said mixture to recover p-dioxanone;
   (d) polymerizing p-dioxanone to form a polymer; and
   (e) forming said polymer into a surgical article.

14. A method as in claim 13 wherein said forming step comprises dehydrogenating diethylene glycol.

15. A method as in claim 13 wherein benzyl bromide is added in an amount from about 0.02 to 0.25 grams per gram of crude reaction product.

16. A method as in claim 13 wherein p-dioxanone is polymerized in the presence of at least one other monomer selected from the group consisting of glycolide, lactide, trimethylene carbonate, dimethyl trimethylene carbonate, caprolactone and polyalkylene oxides.

17. A method as in claim 13 wherein said forming step comprises extruding said polymer into a fiber.

18. A method as in claim 13 wherein said surgical article is a suture.

19. A bioabsorbable polymer obtained by polymerizing a p-dioxanone monomer produced in accordance with the method of claim 1.

20. The polymer of claim 19 wherein the p-dioxanone monomer is copolymerized with another bioabsorbable monomer.

21. The polymer of claim 20 wherein the other bioabsorbable monomer is selected from the group consisting of glycolide, lactide, trimethylene carbonate and caprolactone.

22. An absorbable surgical device fabricated in whole or in part from the polymer of claim 19.

23. An absorbable surgical device fabricated in whole or in part from the polymer of claim 19.

* * * * *